United States Patent
Chen

(10) Patent No.: US 8,592,054 B2
(45) Date of Patent: Nov. 26, 2013

(54) THIOPHENE DERIVATIVES AND ITS APPLICATIONS

(75) Inventor: Shinn-Horng Chen, Taipei (TW)

(73) Assignee: Eternal Chemical Co., Ltd., Kaohsiung (TW)

( * ) Notice: Subject to any disclaimer, the term of this patent is extended or adjusted under 35 U.S.C. 154(b) by 586 days.

(21) Appl. No.: 12/486,307

(22) Filed: Jun. 17, 2009

(65) Prior Publication Data

US 2010/0237771 A1    Sep. 23, 2010

(30) Foreign Application Priority Data

Mar. 23, 2009    (TW) ............................... 98109348 A

(51) Int. Cl.
    *H01L 51/54*    (2006.01)
(52) U.S. Cl.
    USPC ........... 428/690; 428/917; 313/504; 313/505; 313/506; 257/40; 257/E51.05; 257/E51.026; 257/E51.032; 548/418; 548/440
(58) Field of Classification Search
    USPC ...................... 428/690, 917; 257/40, E51.05, 257/E51.026, E51.032; 313/504, 505, 506; 548/440, 418
    See application file for complete search history.

(56) References Cited

U.S. PATENT DOCUMENTS

| | | | | |
|---|---|---|---|---|
| 2003/0055130 | A1* | 3/2003 | Groenendaal et al. | 523/161 |
| 2004/0119049 | A1* | 6/2004 | Heeney et al. | 252/299.3 |
| 2004/0258954 | A1* | 12/2004 | Takasu et al. | 428/690 |

FOREIGN PATENT DOCUMENTS

JP    2000-026451    1/2000

OTHER PUBLICATIONS

Reynolds et. al., Electrochromic Conducting Polymers via Electrochemical Polymerization of Bis(2-(3,4-ethylenedioxy)thienyl) Monomers, 1996, Chemistry Materials, vol. 8, pp. 882-889.*
Zhang, Cheng, et al., "Electropolymerization of alternating phenylene and thiophene electrochromic polymers," *Journal of Chemical Industry and Engineering*, vol. 59, o. S1, pp. 80-83 (Dec. 2008).
Silcoff, Elliad R., et al., "Synthesis of Polymers with Isolated Thiophene-Arylidene-Thiophene Chromophores for Enhanced and Specific Electron/Hole Transport," *Journal of Polymer Science: Part A: Polymer Chemistry*, vol. 39, No. 6, pp. 872-879 (2001).
Turbiez, Mathieu, et al., "Design of Organic Semiconductors: Tuning the Electronic Properties of π-Conjugated Oligothiophenes with the 3,4-Ethylenedioxythiophene (EDOT) Building Block," *Chemistry: A European Journal*, vol. 11, No. 12, pp. 3742-3752 (2005).
Jung, Young Kwan, et al., "Alternating Fluorene Copolymers Containing Isothianaphthene Derivatives: A Study of Their Aggregation Properties and Small Band Gap," *Journal of Polymer Science: Part A: Polymer Chemistry*, vol. 46, No. 11, pp. 3573-3590 (2008).
Guthrie, Daryl A., et al., "Conformation as a Protecting Group: A Regioselective Aromatic Bromination En Route to Complex π-Electron Systems," *Organic Letters*, vol. 10, No. 19, pp. 4323-4326 (2008).
Reynolds, John R., "Electrochromic Polymers and Devices Via Elecropolymerized Low Potential Monomers," *Polymer Preprints*, vol. 37, No. 1, p. 135 (Mar. 1996).

* cited by examiner

*Primary Examiner* — Gregory Clark
(74) *Attorney, Agent, or Firm* — Patterson Thuente Pedersen, P.A.

(57) ABSTRACT

A thiophene derivative, which has a chemical structure of formula (1):

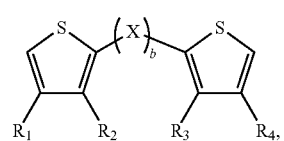

formula (1)

wherein,
X is a substituted or non-substituted $C_6$-$C_{20}$ aromatic or $C_1$-$C_{20}$ aliphatic group;
$R_1$ and $R_2$ are independently H, a $C_1$-$C_{10}$ linear, branched, or cyclic aliphatic group, or connected with the carbon atoms of formula (1) to form a first heterocyclic ring;
$R_3$ and $R_4$ are independently H, a $C_1$-$C_{10}$ linear, branched, or cyclic aliphatic group, or connected with the carbon atoms of formula (1) to form a second heterocyclic ring; and
b is an integer ranging from 1 to 10,
with a proviso that X is not

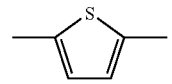

when all of $R_1$, $R_2$, $R_3$ and $R_4$ are H.

7 Claims, No Drawings

THIOPHENE DERIVATIVES AND ITS APPLICATIONS

CROSS-REFERENCES TO RELATED APPLICATIONS

This application claims priority to Taiwan Patent Application No. 098109348 filed on Mar. 23, 2009, the disclosures of which are incorporated herein by reference in their entirety.

BACKGROUND OF THE INVENTION

1. Field of the Invention

The present invention provides a thiophene derivative. In particular, the present invention provides a thiophene derivative suitable for use as an organic light-emitting material or a conductive material.

2. Descriptions of the Related Art

Currently, light-emitting diodes (LEDs) are commonly used. For example, most traffic lights and large monitors use inorganic LEDs. As for the organic material-based LEDs, they can be manufactured into displays. Also, it has been predicted that organic LEDs will be the mainstream of medium-size or mini-size displays in the next generation due to their advantages such as self-luminous property, high response rate, low power consumption, large viewing angle, light weight, thin thickness, high brightness, full-color, and ability to display animated images.

Organic light-emitting diodes (OLEDs), first published by Kodak in the 1980s, are display elements that use the electroluminescence of an organic light-emitting material, i.e., a property that shows reversible color change to provide display effects when a voltage or current is applied. The OLED is mostly composed of a pair of electrodes and an organic light emitting layer, wherein the organic light emitting layer includes a light emitting material.

In 1990s, D. D. Bradley found another conjugated polymer with electroluminescence, i.e., poly(p-phenylene vinylene). The conjugated polymers have since been applied in LEDs. The conjugated polymers are polymers where the main chain thereof is composed of mutually connected double bonds and single bonds. Such polymers have special photoelectric properties, and have been the focal point of the development of organic semiconductor materials.

Compared to inorganic LEDs, the polymer LEDs can be prepared more easily. Among the numerous conjugated polymers, polythiophene and its derivatives are especially representative conjugated polymers. In addition to superior stability and thermal stability, polythiophene and its derivatives also have electrochromic properties, and thereby can be used as conductive materials or light emitting materials. The conductive/light emitting materials are widely used in the electro-optical field, e.g., as conductive materials required for thin film transistors (TFTs), capacitors, solar cells, or fuel cells, or as light emitting materials of OLEDs. In addition, they can be used in anti-statics, sealing applications etc.

In the electro-optical field, the "relative quantum yield" is usually a basis for judging the luminous efficiency of electro-optical materials. In other words, electro-optical materials with a higher relative quantum yield demonstrate better luminous efficiency, while electro-optical materials with a lower relative quantum yield demonstrate poor luminescent efficiency. The relative quantum yield is measured by using Coumadine having a quantum yield of 0.55 under $10^{-5}$ M sulfuric acid solution as a standard with UV-absorbing spectrum and fluorescence emission spectrum. The relative quantum yields can be obtained from the ratio of the integration values of the above two spectrums and the refractive index of the testing solution.

The sulfur element in the structure of the conductive polymers of polythiophene and its derivatives will lower the relative quantum yield, and thereby lower the application efficiency. In view of this, the inventor of the present invention conducted a lot of research and found that the relative quantum yield of polythiophene or its derivatives can be increased to improve the applicability by doping an aromatic ring or heterocyclic ring.

Thus, the present invention provides a thiophene derivative, which has a better relative quantum yield. Also, the conjugation length can be changed by changing the structure of the thiophene derivative to change the color of luminescence, and thereby, the thiophene derivative can be more widely used. The longer the conjugation length is, the longer the wavelength of the emitted light (i.e., red shift) and the smaller the band gap (E) will be. On the contrary, the shorter the conjugation length is, the shorter the wavelength of the emitted light (i.e., blue shift) and the greater the band gap will be. The band gap can be obtained by the formula $E=hc/\lambda=1240/\lambda$, wherein $\lambda$ is the wavelength at the intersection point of X-axis (wavelength axis) and the absorption peak of the longest wavelength of the UV spectrum. The conjugation length of the thiophene derivative can be changed by designing its molecular structure to adjust the color of luminescence, and thus, the thiophene derivative can be more widely used. Moreover, the solubility of the thiophene derivative of the present invention is improved in the presence of an aromatic ring, and thus, is more convenient for use.

SUMMARY OF THE INVENTION

One objective of this invention is to provide a thiophene derivative, which has a chemical structure of formula (1):

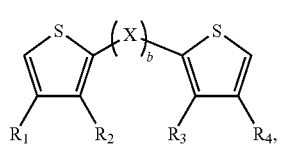

formula (1)

wherein,

X is a substituted or non-substituted $C_6$-$C_{20}$ aromatic or $C_1$-$C_{20}$ aliphatic group;

$R_1$ and $R_2$ are independently H, a $C_1$-$C_{10}$ linear, branched, or cyclic aliphatic group, or connected with the carbon atoms of formula (1) to form a first heterocyclic ring;

$R_3$ and $R_4$ are independently H, a $C_1$-$C_{10}$ linear, branched, or cyclic aliphatic group, or connected with the carbon atoms of formula (1) to form a second heterocyclic ring; and b is an integer ranging from 1 to 10, with a proviso that X is not

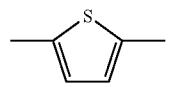

when all of $R_1$, $R_2$, $R_3$ and $R_4$ are H.

Another objective of this invention is to provide a conductive material comprising the above thiophene derivative, wherein the conductive material is used as a capacitor material or sensitizing dye of solar cells.

Yet a further objective of this invention is to provide an organic light-emitting material including the above thiophene derivative.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

The thiophene derivative according to the present invention has a chemical structure of formula (1):

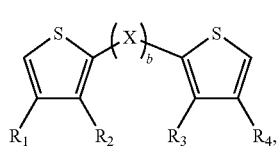

formula (1)

wherein,
X is a substituted or non-substituted $C_6$-$C_{20}$ aromatic or $C_1$-$C_{20}$ aliphatic group;
$R_1$ and $R_2$ are independently H, a $C_1$-$C_{10}$ linear, branched, or cyclic aliphatic group, or connected with the carbon atoms of formula (1) to form a first heterocyclic ring;
$R_3$ and $R_4$ are independently H, a $C_1$-$C_{10}$ linear, branched, or cyclic aliphatic group, or connected with the carbon atoms of formula (1) to form a second heterocyclic ring; and
b is an integer ranging from 1 to 10,
with a proviso that X is not

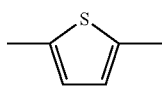

when all of $R_1$, $R_2$, $R_3$ and $R_4$ are H.

Preferably, X of formula (1) is selected from a group consisting of the following formulas (2) to (10):

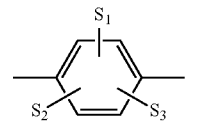

formula (2)

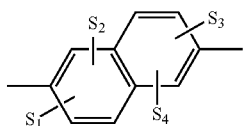

formula (3)

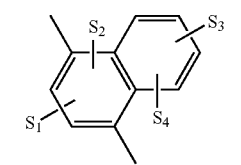

formula (4)

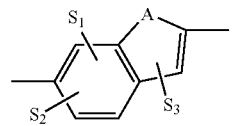

formula (5)

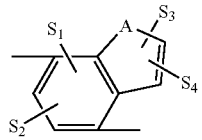

formula (6)

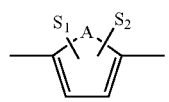

formula (7)

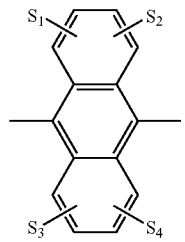

formula (8)

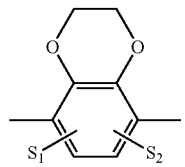

formula (9)

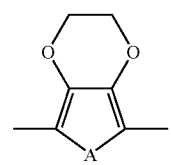

formula (10)

wherein,
A is S, O, N or Se; and
$S_1$, $S_2$, $S_3$ and $S_4$ are independently H, a $C_1$-$C_8$ alkyl group or a $C_1$-$C_8$ alkoxy group.

According to the preferred embodiments of the present invention, in formula (1), X is selected from a group consisting of

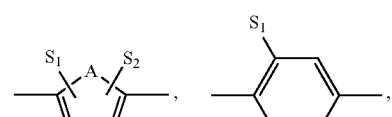

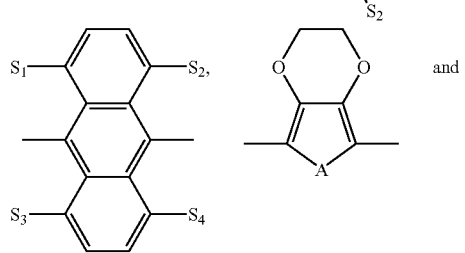

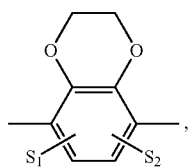

wherein A is S, O, N or Se, and $S_1$, $S_2$, $S_3$ and $S_4$ are independently H or a $C_1$-$C_3$ alkyl group; $R_1$, $R_2$, $R_3$ and $R_4$ are independently H, $CH_3$, $C_2H_5$, $OCH_3$, $OC_2H_5$, $OC_2H_3$, $OC_3H_5$ or $C_3H_7$; and b is an integer ranging from 1 to 3.

More preferably, in formula (1), X is

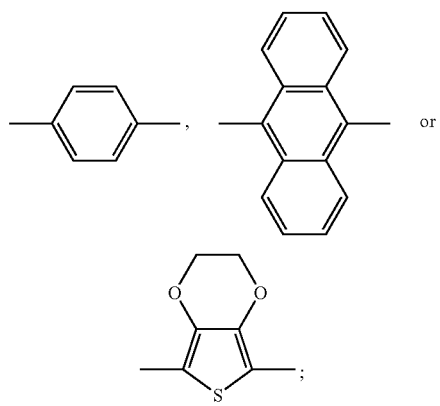

$R_1$, $R_2$, $R_3$ and $R_4$ are independently H or $CH_3$; and b is 1.

According to the other preferred embodiments of the present invention, in formula (1), X is selected from a group consisting of

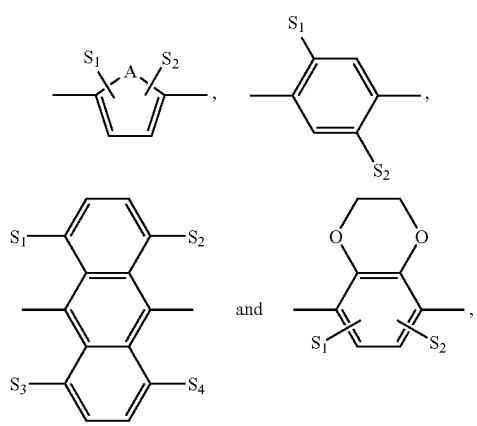

wherein A is S, O, N or Se, and $S_1$, $S_2$, $S_3$ and $S_4$ are independently H or a $C_1$-$C_3$ alkyl group; $R_1$ and $R_2$ are connected with the carbon atoms of formula (1) to form a first heterocyclic ring; $R_3$ and $R_4$ are connected with the carbon atoms of formula (1) to form a second heterocyclic ring; and b is an integer ranging from 1 to 3. The first heterocyclic ring and the second heterocyclic ring are further illustrated below through the following formula (1'):

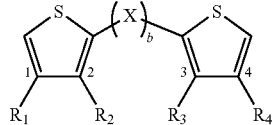

formula (1')

$R_1$ and $R_2$ form a 3 to 10 element first heterocyclic ring with carbon atoms 1 and 2 of formula (1') and $R_3$ and $R_4$ form a 3 to 10 element second heterocyclic ring with carbon atoms 3 and 4 of formula (1'). The number of the hetero-atoms of the first heterocyclic ring or the second heterocyclic ring ranges from 1 to 3, and the hetero-atom can be N, O or S, preferably O.

In other preferred embodiments of the present invention, more preferably, X is selected from a group consisting of

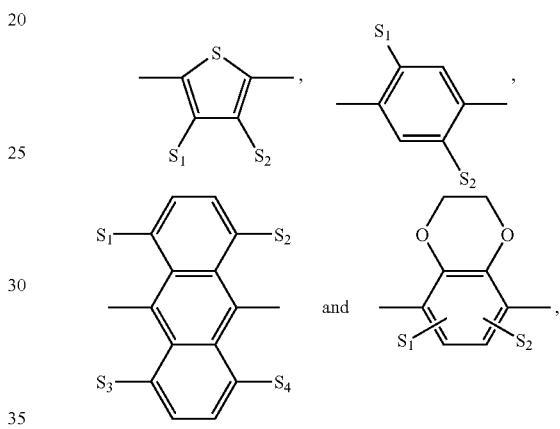

wherein $S_1$, $S_2$, $S_3$ and $S_4$ are independently H or $CH_3$; the first heterocyclic ring and/or the second heterocyclic ring are/is

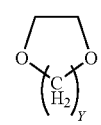

and Y is an integer ranging from 0 to 6; and b is 1.

In other preferred embodiments of the present invention, most preferably, X is

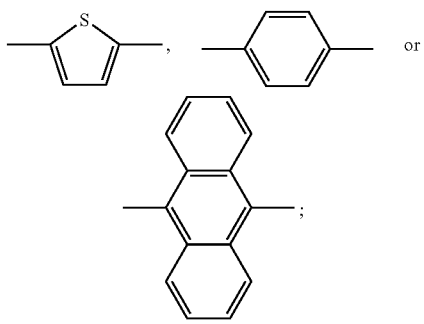

the first heterocyclic ring and/or the second heterocyclic ring are/is

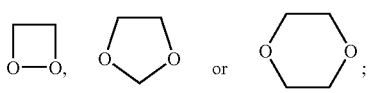

and b is 1.

The thiophene derivatives of the present invention can be prepared according to the synthesis method familiar to people with ordinary skill in the art. For example, the thiophene derivatives of the present invention may be prepared by the following method: reacting halogenated thiophene with Mg powders in a solvent of ethyl ether or tetrahydrofuran to generate Grignard reagent (alkyl halogenated magnesium, R—MgX); and then reacting the Grignard reagent with a halogenated aliphatic or halogenated aromatic to generate the thiophene derivatives of the present invention. The above illustration may be represented by the following equations:

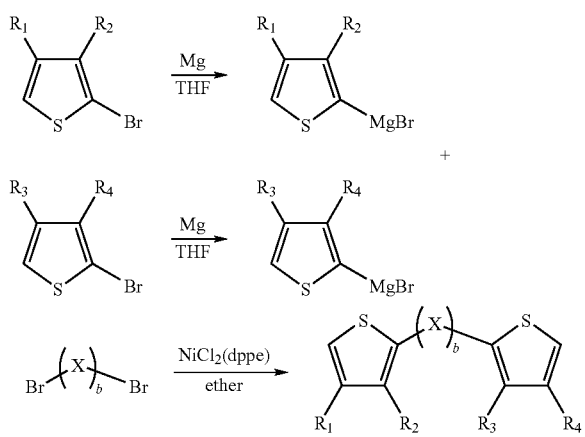

The thiophene derivatives of the present invention have improved relative quantum yield and are especially suitable for use as conductive materials. Thus, the present invention also relates to a conductive material comprising the thiophene derivative of formula (1). The conductive material can be used as, for example, a capacitor material or sensitizing dye of solar cell materials.

The thiophene derivatives of formula (1) according to the present invention are also suitable for use in an organic light-emitting material. The organic light-emitting material comprising the thiophene derivative of formula (1) can be applied in an OLED element as a material of light emitting layer and provides well luminous efficiency. Furthermore, said organic light emitting material can be incorporated into an OLED element as a material of light emitting layer or a portion of the material of light emitting layer by any familiar method in this field. Namely, the organic light-emitting material of the present invention can be mixed with other materials in various ratios and then applied on the elements as a material of the light emitting layer of an organic light emitting element. The luminous efficiency of OLED elements can be improved and the luminescent color can be regulated when the light emitting material is doped in light-emitting. For example, through doping techniques, the organic light-emitting material comprising the thiophene derivative of formula (1) of the present invention may play the role of the host of energy, or the guest of energy as a light emitting dopant.

COMPARATIVE EXAMPLE

According to the following equation, the thiophene derivative of formula (11) was prepared from the reactants in a molar ratio of 2 (up to 2.1):1 in the presence of a catalyst of 5 wt % $NiCl_2$ (dppe) (1,2-bis-(diphenylphosphino)ethane) and a solvent of ethyl ether.

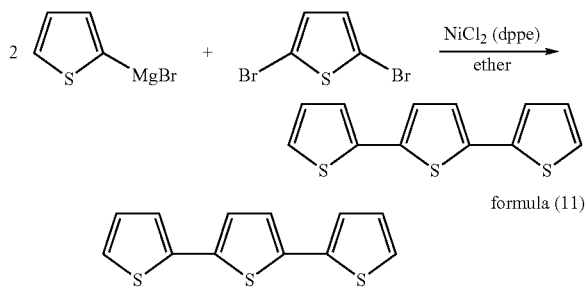

formula (11)

The molecular weight of the prepared compound was 248. The identified location of hydrogen spectrum was characterized by $^1$H NMR (solvent: $CDCl_3$, 400 MHz, ppm) and the chemical shift (δ) was as follows: 7.24-7.22 (d, Ar—H 2H), 7.19-7.18 (d, Ar—H 2H), 7.09 (s, Ar—H 2H), 7.04-7.02 (m, Ar—H 2H).

Example 1

According to the following equation, the thiophene derivative of formula (12) was prepared from the reactants in a molar ratio of 2 (up to 2.1):1.

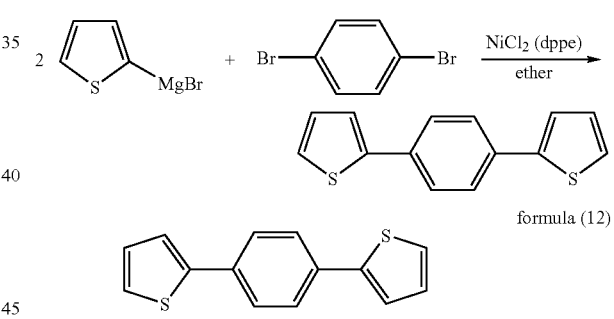

formula (12)

The molecular weight of the prepared compound was 242. The identified location of hydrogen spectrum was characterized by $^1$H NMR (solvent: $CDCl_3$, 400 MHz, ppm) and the chemical shift (δ) was as follows: 7.63 (s, Ar—H 4H), 7.36-7.35 (d, Ar—H 2H), 7.31-7.30 (d, Ar—H 2H), 7.12-7.09 (m, Ar—H 2H).

Example 2

According to the following equation, the thiophene derivative of formula (13) was prepared from the reactants in a molar ratio of 2 (up to 2.1):1.

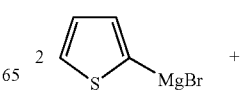

-continued

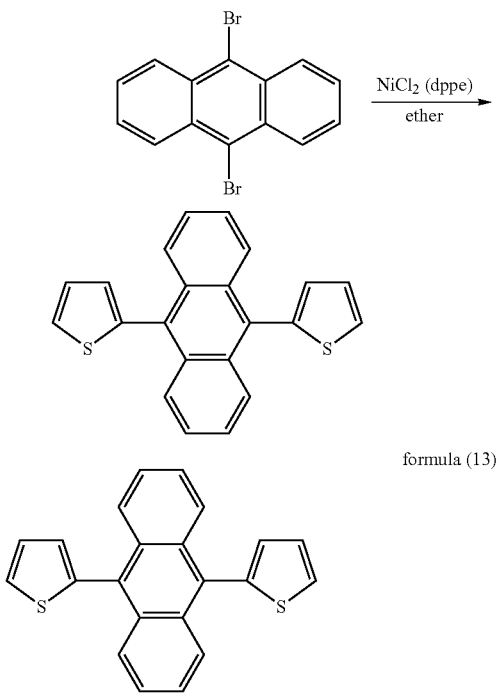

formula (13)

The molecular weight of the prepared compound was 342. The identified location of hydrogen spectrum was characterized by $^1$H NMR (solvent: CDCl$_3$, 400 MHz, ppm) and the chemical shift (δ) was as follows: 7.90-7.87 (m, Ar—H 4H), 7.65-7.63 (m, Ar—H 2H), 7.43-7.41 (m, Ar—H 4H), 7.35-7.32 (m, Ar—H 2H), 7.24-7.23 (m, Ar—H 2H).

Example 3

According to the following equation, the thiophene derivative of formula (14) was prepared from the reactants in a molar ratio of 2 (up to 2.1):1.

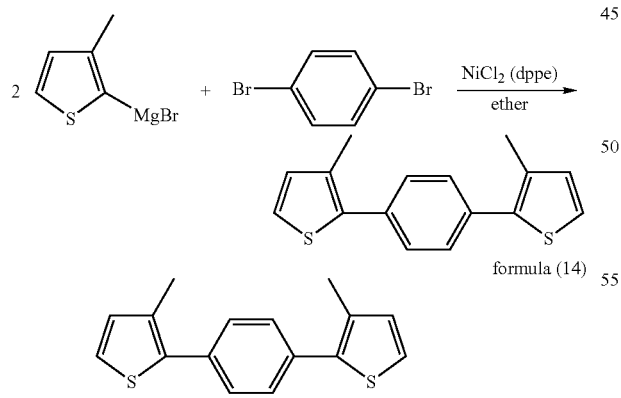

formula (14)

The molecular weight of the prepared compound was 270. The identified location of hydrogen spectrum was characterized by $^1$H NMR (solvent: CDCl$_3$, 400 MHz, ppm) and the chemical shift (δ) was as follows: 7.52 (s, Ar—H 4H), 7.24-7.23 (d, Ar—H 2H), 6.96-6.95 (d, Ar—H 2H), 2.38 (s, —CH$_3$ 6H).

Example 4

According to the following equation, the thiophene derivative of formula (15) was prepared from the reactants in a molar ratio of 2 (up to 2.1):1.

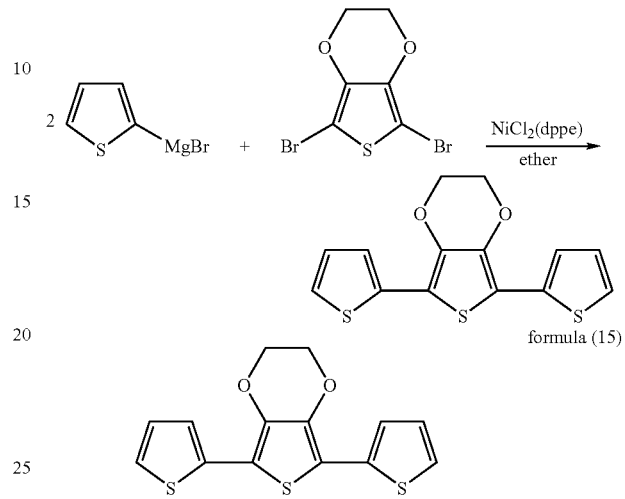

formula (15)

The molecular weight of the prepared compound was 306. The identified location of hydrogen spectrum was characterized by $^1$H NMR (solvent: CDCl$_3$, 400 MHz, ppm) and the chemical shift (δ) was as follows: 7.25-7.22 (m, Ar—H 2H), 7.13-7.08 (m, Ar—H 4H), 4.32-4.38 (m, —OCH$_2$— 4H).

Example 5

According to the following equation, the thiophene derivative of formula (16) was prepared from the reactants in a molar ratio of 2 (up to 2.1):1.

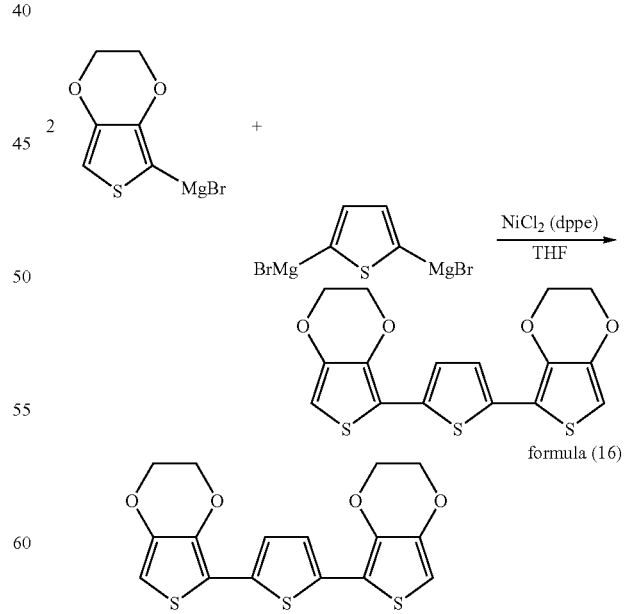

formula (16)

The molecular weight of the prepared compound was 364. The identified location of hydrogen spectrum was characterized by $^1$H NMR (solvent:CDCl$_3$, 400 MHz, ppm) and the chemical shift (δ) was as follows: 7.24-7.22 (m, Ar—H 2H), 7.06-6.96 (m, Ar—H 2H), 4.41-4.39 (m, —OCH$_2$-4H), 4.37-4.36 (m, —OCH$_2$-4H).

Efficiency Test

Coumadine, having a quantum yield of 0.55 under 10$^{-5}$ M sulfuric acid solution, was taken as a standard. The relative quantum yields of the thiophene derivatives prepared from Comparative Example and Examples 1 to 5 were measured and recorded in Table 1.

TABLE 1

|  | Comparative example | Example 1 | Example 2 | Example 3 | Example 4 | Example 5 |
|---|---|---|---|---|---|---|
| Relative quantum yield (%) | 16.2 | 37.8 | 51.6 | 44.9 | 24.2 | 28 |

As seen in Table 1, compared to Comparative Example, the thiophene derivatives of Examples 1 to 5 (doped with aromatic rings or heterocyclic rings) have better relative quantum yields. In other words, the thiophene derivatives provided by the present invention provide better relative quantum yields indeed, and thereby, can be applied more widely.

Given the above, the thiophene derivatives provided by the present invention certainly have improved relative quantum yields and industrial applicability.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A thiophene derivative, which has a chemical structure of formula (1):

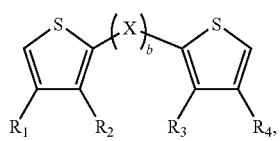

formula (1)

wherein X is

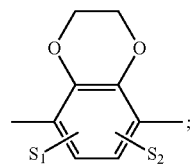

wherein S$_1$ and S$_2$ are independently H or C$_1$-C$_3$ alkyl;

R$_1$ and R$_2$ are connected with the carbon atoms of formula (1) to form a first heterocyclic ring;
R$_3$ and R$_4$ are connected with the carbon atoms of formula (1) to form a second heterocyclic ring; and
b is an integer ranging from 1 to 3.

2. The thiophene derivative of claim 1, wherein X is

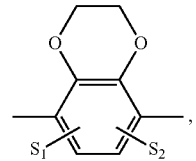

wherein S$_1$ and S$_2$ are independently H or C$_1$-C$_3$ alkyl;
the first heterocyclic ring or the second heterocyclic ring is

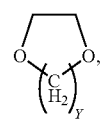

and y is an integer ranging from 0 to 6; and
b is 1.

3. A conductive material, comprising the thiophene derivative of claim 1.

4. An organic light emitting material, comprising the thiophene derivative of claim 1.

5. A thiophene derivative, which has a chemical structure of formula (1):

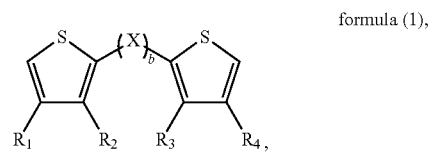

formula (1), wherein X is

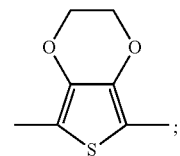

R$_1$, R$_2$, R$_3$ and R$_4$ are independently H or CH$_3$; and
b is 1.

6. A conductive material, comprising the thiophene derivative of claim 5.

7. An organic light emitting material, comprising the thiophene derivative of claim 5.

* * * * *